(12) United States Patent
Belohlavek et al.

(10) Patent No.: US 8,308,646 B2
(45) Date of Patent: Nov. 13, 2012

(54) TRAINABLE DIAGNOSTIC SYSTEM AND METHOD OF USE

(75) Inventors: Marek Belohlavek, Rochester, MN (US); Eileen M. McMahon, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 1508 days.

(21) Appl. No.: 11/405,289

(22) Filed: Apr. 17, 2006

(65) Prior Publication Data

US 2006/0235319 A1    Oct. 19, 2006

Related U.S. Application Data

(60) Provisional application No. 60/672,493, filed on Apr. 18, 2005.

(51) Int. Cl.
*A61B 5/02* (2006.01)

(52) U.S. Cl. ........ 600/483; 600/407; 600/410; 600/484; 600/481; 600/485; 600/509; 600/528; 600/513

(58) Field of Classification Search ................ 600/509, 600/528, 513, 407, 410, 481–485
See application file for complete search history.

(56) References Cited

U.S. PATENT DOCUMENTS

| | | |
|---|---|---|
| 5,596,993 A | 1/1997 | Oriol et al. |
| 6,135,966 A | 10/2000 | Ko |
| 2002/0045809 A1* | 4/2002 | Ben-Haim ................ 600/374 |
| 2003/0013963 A1* | 1/2003 | Bjaerum et al. ........... 600/443 |
| 2003/0093003 A1 | 5/2003 | Watrous et al. |
| 2005/0020903 A1* | 1/2005 | Krishnan et al. .......... 600/407 |

OTHER PUBLICATIONS

Theodore P. Abraham et al; Time to Onset of Regional Relaxation: Feasibility and Utility of a Novel Index of Regional Myocardial Function by Strain Rate Imaging; JACC; Aug. 16, 2006; pp. 1531-1537; vol. 39, No. 9, 2002.

C. Tranulis et al; Estimation of Pulmonary Arterial Pressure by A Neural Network Analysis Using Features Based on Time-Frequency Representations of The Second Heart Sound; Med. & Biol. Eng. & Comp. 2002, vol. 40, pp. 205-212.

(Continued)

*Primary Examiner* — Brian Casler
*Assistant Examiner* — Joel Lamprecht
(74) *Attorney, Agent, or Firm* — Quarles & Brady, LLP; Jack M. Cook

(57) ABSTRACT

A trainable, adaptable system for analyzing functional or structural clinical data can be used to identify a given pathology based on functional data. The system includes a signal processor that receives functional data from a device monitoring a subject and normalizes the functional data over at least one cycle of functional data. The system also includes a neural network having a plurality of weights selected based on predetermined data and receiving and processing the normalized functional data based on the plurality of weights to generate at least one metric indicating a degree of relation between the normalized functional data to the predetermined data. A diagnostic interpretation module is included for receiving the at least one metric from the neural network and classifying the functional data as indicative of the given pathology or not indicative of the given pathology based on a comparison of the at least one metric to at least one probability distribution of a likelihood of the given pathology.

19 Claims, 4 Drawing Sheets

OTHER PUBLICATIONS

Chris D. Nugent et al; Prediction Models in the Design Neural Network Based ECG Classifiers: A Neural Network and Genetic Programming Approach; BMC Medical Informalities and Decision Making 2002; pp. 1-6.

Piero Tortoli et al; Extraction of Endocardial Boundary From Echocardiographic Images by Means of the Kohonen Self-Organizing Map; Accoustical Imaging, vol. 22, pp. 197-202.

Karl Heinz Hohne et al; Visualization in Biomedical Computing; 4th International Conference, VBC '96; Hamburg, GR; Sep. 22-25, 2006; pp. 247-252.

Julia H. Smith et al; The Application of an Artificial Neural Network to Doppler Ultrasound Waveforms for the Classification of Arterial Disease; International Journal of Clinical Monitoring and Computing 13:85-91, 1996.

Karsten Sternickel; Automatic Pattern Recognition in ECG Time Series; Computer Methods and Programs in Biomedicine; 68 (2002) 109-115.

Costas Paploukas et al, An Ischemia Detection Method Based on Artificial Neural Networks; Artificial Intelligence in Medicine, Feb. 2002, vol. 24, Issue 2; pp. 167-178.

A. Stassopoulou, et al.; Correspondence Between Bayesian and Neural Networks, International Journal of Pattern Recognition and Artificial Intelligence, vol. 12, No. 7, (1998) 901-920, Surrey, United Kingdom, World Scientific Publishing Company, Singapore.

Theodore P. Abraham, M.D., et al., Time to Onset of Regional Relaxation: Feasibility, Variability and Utility of a Novel Index of Regional Myocardial Function by Strain Rate Imaging, Journal of American College of Cardiology, vol. 39, No. 9, 2002; Published by Elsevier Science Inc., Rochester, Minnesota.

McMahon et al, Classification of acute myocardial ischemia by artificial neural network using echocardiographic strain waveforms, Computers in Biology and Medicine 38 (2008) 416-424.

\* cited by examiner

TRAINABLE DIAGNOSTIC SYSTEM AND METHOD OF USE

CROSS-REFERENCE TO RELATED APPLICATIONS

This application is based on U.S. Provisional Patent Application Ser. No. 60/672,493 filed on Apr. 18, 2005, and entitled "TRAINABLE IMAGING SYSTEM".

STATEMENT REGARDING FEDERALLY SPONSORED RESEARCH

This invention was made with government support under Grant No. NIH HL70363. The United States Government has certain rights in this invention.

BACKGROUND OF THE INVENTION

The present invention relates generally to a system and method for analyzing functional imaging data to determine indicators of various pathologies with increased speed and accuracy. More particularly, the present invention relates to a system and method for evaluating a full spectrum of functional imaging data, such as cardiac ultrasound images or entire echocardiogram waveforms, to determine indicators of pathologies such as ischemia.

Functional imaging has traditionally included such modalities as ultrasound and nuclear imaging systems, including positron emission tomography (PET) systems and single photon emission computed tomography (SPECT) systems. In recent years, additional techniques have evolved, such as functional magnetic resonance imaging (fMRI), tagged MRI, and magnetoencephalography (MEG). Furthermore, echocardiograms have been utilized as another feedback component that can be used alone or in combination with these functional imaging techniques.

Heart disease has a very high incidence as well as a high rate of early mortality. The use of functional imaging systems and, in particular, echocardiography has become widespread as a diagnosis tool for identifying symptoms of heart disease. For example, the real-time nature of echocardiograms has allowed for the observation of myocardial motion and its synchronicity or the lack thereof. Furthermore, Doppler analysis has been indirectly used with various functional imaging systems to analyze heart valve function by measuring blood flow and observing turbulence.

Continual advancements in these functional imaging systems have enabled the identification of symptoms of heart disease or other ailments. For example, new analysis techniques have been developed that help identify changes in cardiac function (cyclic cardiac muscle deformations) in disease. In particular, by analyzing echocardiogram waveforms obtained before and after ischemia, physicians and technicians have been able to identify features within echocardiogram waveforms that are indicative of altered myocardial deformations. These alterations can then be related to disease symptoms or pathologies.

However, due to the complexity and variability of these waveforms in both normal hearts at their baseline condition and in the same hearts after occlusion of a coronary artery, the evaluation and analysis of these waveforms is extremely intensive and requires highly skilled determinations to be made in real or near real-time. Hence, a physician or technician must evaluate a baseline echocardiogram waveform and compare it to an echocardiogram waveform following ischemia and, in substantially real-time, to determine indicators of myocardial deformations or other symptoms of similar pathologies.

To make such analysis manageable, functional analysis methods rely on identifying changes in myocardial deformation expressed as strain waveforms derived from ultrasound data. However, movement of the myocardium includes a multitude of individual myocytes working in different directions in layers of the muscle, and timing of each contraction is not simultaneous throughout the heart due to differing electrical and mechanical activation of distinct myocardial regions. Thus, strain waveforms, even for normal regions of myocardium, have a large variability. Since the movement of the myocardium is extremely complex, functional analysis has been limited to merely comparing peaks or crossover points in the waveforms. Hence, only a small fraction of the data contained in the waveforms is considered during analysis.

Predominantly, these parameters are measurements of strain rate or strain magnitude, especially peaks during particular phases of the heart cycle, or alternatively, timings between selected events have been used. Examples of the latter, from both clinical and animal research studies, include the time from the ECG R-wave to peak negative strain and timing to various crossover points as strain or strain rate changes from positive to negative or vice versa. However, the strain waveform is rich in information about local myocardial function throughout the cardiac cycle and limiting the analysis to these particular events disregards a wealth of information that could be indicative of a particular pathology.

Furthermore, to perform the prescribed analysis, clinicians have been required to rely upon experience and observational skills to describe regional myocardial movements and identify segments of the heart that might be normal or ischemic. As such, considerable stress is placed upon the evaluator to simultaneously evaluate the waveforms and identify features within these complex and constantly varying waveforms that may indicate myocardial ischemia or other pathologies. As such, traditional diagnosis methods can be extremely subjective and prone to human error.

Therefore, it would be desirable to have a system and method for analyzing a wide variety of functional imaging data to determine indicators of various pathologies with increased speed and accuracy. For example, it would be desirable to have a system and method to aid in the interpretation and evaluation of a full spectrum of functional imaging data, such as cardiac ultrasound images or entire echocardiogram waveforms, to determine indicators of pathologies such as ischemia.

SUMMARY OF THE INVENTION

The present invention overcomes the aforementioned drawbacks by providing a system and method for probabilistically analyzing a full range of functional data to automatically categorize a waveform as normal or abnormal. The present invention analyzes the entire functional waveform through a cardiac cycle, as opposed to merely reviewing and comparing peaks or crossover points, to determine whether the cardiac waveform includes indicia of ischemic myocardium.

According to one embodiment of the present invention, a system for analyzing functional data to identify a given pathology is disclosed that includes a signal processor receiving functional waveform information from a device monitoring a cardiac cycle of a subject and normalizing the functional waveform over at least one portion of the functional waveform. The system also includes a neural network having a plurality of weights selected based on predetermined data and receiving and processing the normalized functional waveform based on the plurality of weights to generate at least one metric indicating a degree of relation between the normalized functional waveform and the predetermined data. A diagnostic interpretation module is included for receiving the at least one metric from the neural network and classifying the functional waveform as indicative of the given pathology or not indicative of the given pathology based on a comparison of the at least one metric to at least one probability distribution of a likelihood of the given pathology.

Various other features and advantages of the present invention will be made apparent from the following detailed description and the drawings.

DETAILED DESCRIPTION OF THE PREFERRED EMBODIMENT

The present invention provides a trainable system capable of assessing the probability of normal and abnormal segmental left ventricle (LV) function from patterns of local mechanical waveforms. In particular, the present invention is capable of performing the classification and analysis of a variety of data to perform cardiac mechanical function analysis in noisy and discontinuous LV borders in echo images.

Figure 1:
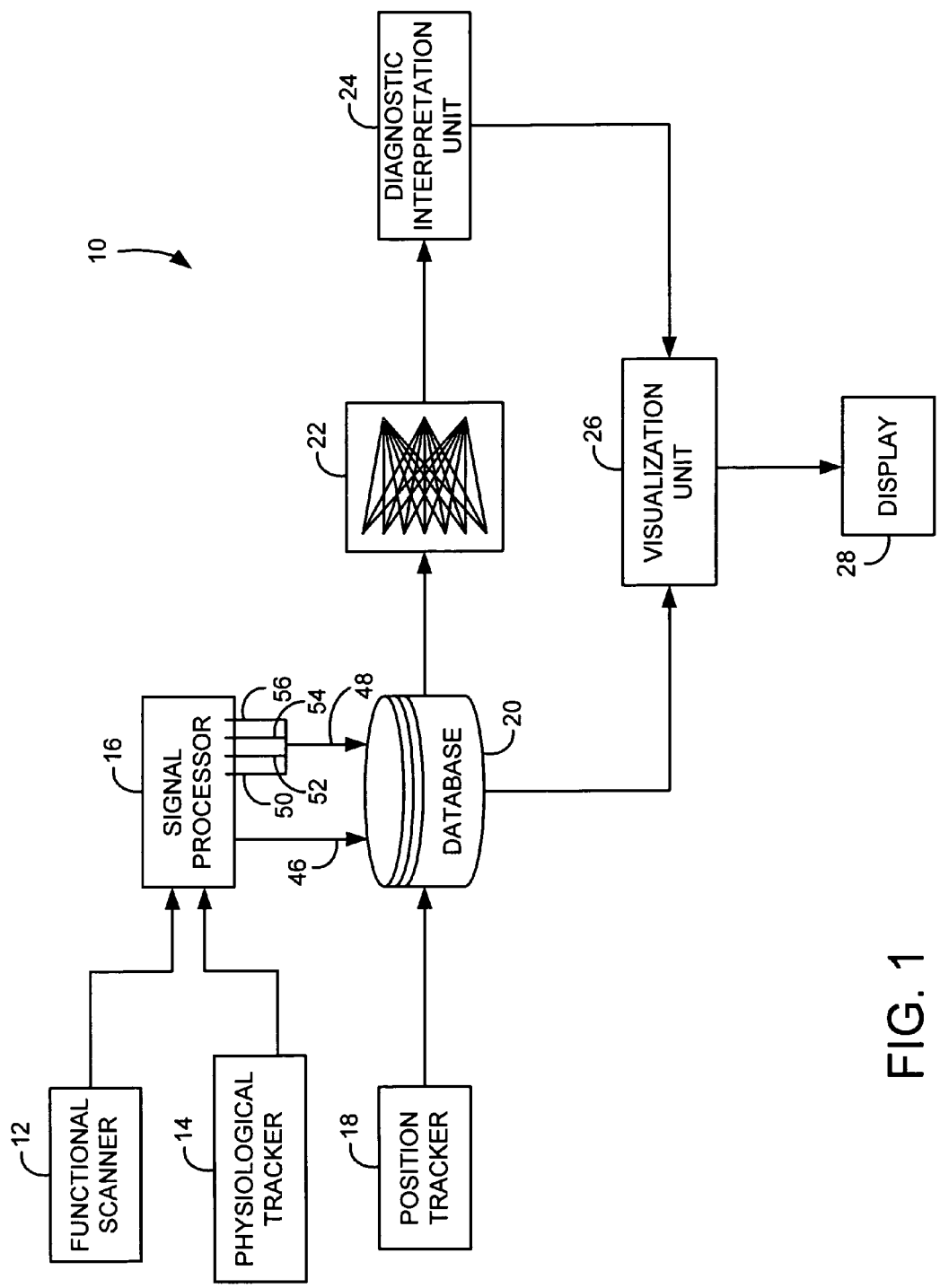
FIG. 1 is a schematic illustration of a preferred embodiment of a trainable diagnostic system in accordance with the present invention.

Referring to FIG. 1, a trainable diagnostic system 10 includes a functional scanner 12 and physiological tracker 14 that provide data to a signal processor 16. The signal processor 16 along with a position tracker 18 provides data that is stored in a database 20 and then delivered to a neural network (NN) 22. As will be described, the NN 22 processes the data received from the database 20 and provides a weighted/analyzed output to a diagnostic interpretation unit 24 that, along with the database 20, provides information to a visualization unit 26 to deliver a graphic display 28.

Figure 2:
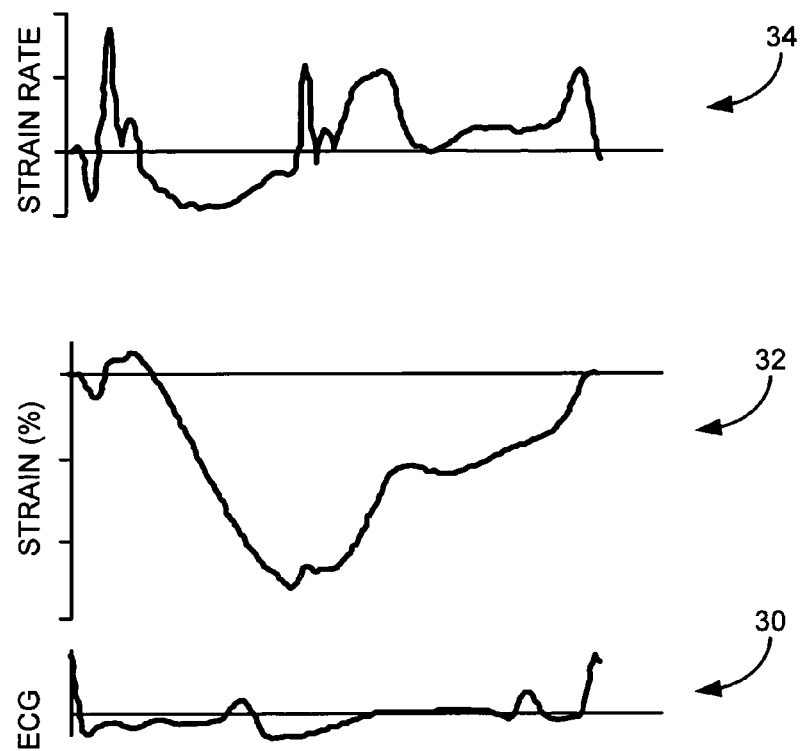
FIG. 2 is a set of graphs showing an ECG waveform, strain waveform, and strain rate waveform acquired using the trainable diagnostic system of FIG. 1.

In the preferred embodiment, the functional scanner 12 is an echocardiographic scanner that allows measurement and tracking of basic cardiac information, such as thickness, dimensional, and radius data, and generates an ECG waveform 30, such as set forth in FIG. 2. Additionally, the functional scanner may be capable of generating a strain waveform 32 and/or strain rate (SR) waveform 34.

When evaluating the heart, "strain" refers to the relative magnitude of regional myocardial deformation. In other words, strain is the relative change in length (longitudinal view) or thickness (transverse view) of a myocardial segment expressed as a percentage of its original length. More particularly, myocardial strain 32 is expressed as a fraction or a percentage of the end-diastolic status and can be calculated by numerical integration of strain rates over a period of one cardiac cycle (i.e., one R-R interval within the ECG waveform 30). Myocardial strain rate 34 is estimated by tissue Doppler echo from discrete velocities, where tissue Doppler echo provides a single dimensional component of myocardial deformation along the ultrasound beam axis and; therefore, the measured deformation magnitudes are angle-dependent. Hence, strain is calculated as:

$$S = \int_{t_0}^{t_T} SR dt,$$

where $t_0$ and $t_T$ are time points of the start and end of the cardiac cycle. Accordingly, strain rate is calculated as:

$$SR \approx \frac{(V_r - V_{r+\Delta r})}{\Delta r},$$

where $\Delta r$ is an offset of approximately 5 to 10 millimeters (mm) along the beam, while $V_r$ and $V_{r+\Delta r}$ are velocity points located $\Delta r$ apart. Strain rate carries units of $s^{-1}$.

Figure 3A:
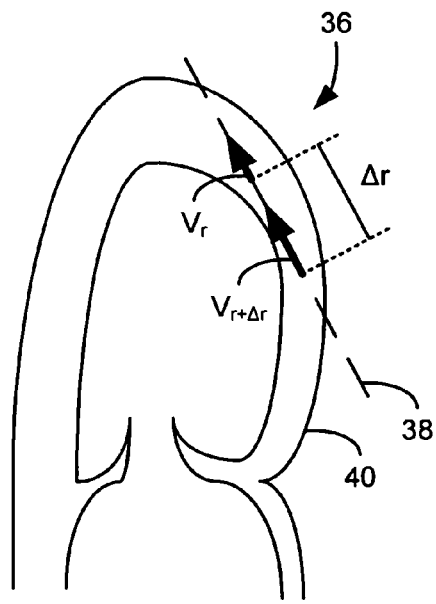
FIG. 3a is a cross-sectional view of a left ventricle of a heart showing metrics used and calculated by the trainable diagnostic system of FIG. 1 to perform diagnostic analysis.

Referring to FIG. 3a, the components used to calculate longitudinal strain rate can be seen by reviewing the left ventricle 36. Here, an axis of a projected ultrasound beam 38 passes through a ventricular wall 40. Along the projected ultrasound beam 38 are velocity vectors $V_r$ and $V_{r+\Delta r}$ that are separated by the value $\Delta r$.

Figure 3B:
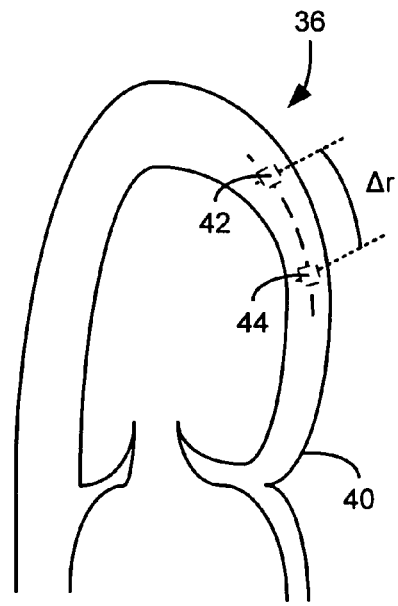
FIG. 3b is a cross-sectional view of a left ventricle of a heart showing speckles tracked using the trainable diagnostic system of FIG. 1.

During evaluation processing, segments are selected from 2D images acquired by the functional scanner 12 of FIG. 1 and their cyclic deformations (compression and expansion strains) are followed. Strains can be calculated from 1D ultrasound Doppler velocities, $V_r$ and $V_{r+\Delta r}$, separated by the value $\Delta r$ (FIG. 3a) or by a 2D speckle-tracking algorithm (FIG. 3b), where two small regions 42, 44 are identified and serve for identification of the velocity vectors.

The reference length for percentage of strain is set at the time point in the heart cycle of end-diastole. Although a distinct difference within waveforms may be visually perceivable, the variety of magnitudes and timings typically vary significantly in both the baseline and ischemic waveforms. Accordingly, the position tracker 18 of FIG. 1 provides ultrasonic beam axis projection and, thus, information about the segment being imaged that, as will be described, is used to segment the derived waveforms and reconstruct visual feedback.

Referring again to FIG. 1, as stated, the physiological tracker 14 may be configured to generate an ECG waveform, a pressure waveform, or the like throughout a cardiac cycle. This information serves as a reference that indicates cardiac phase throughout the cardiac cycle. As stated above, the information produced by the functional scanner 12 and the physiological tracker 14 is delivered to a signal processor 16. The signal processor 16 is performs amplitude normalization, provides temporal resampling, determines strain, and performs low-pass filtering.

In operation, a user measures, for example, time to relaxation ($T_R$) interval, which is delimited by the R-wave location on the ECG waveform and the point of zero-crossing to relaxation on the strain rate waveform. Responsive thereto, the signal processor 16 measures the $T_R$ interval exactly and normalizes the amplitudes of the waveforms based on a resting heart rate. The $T_R$ interval changes from rest to stress by approximately −34±10% in normal and −12 (±18%) in ischemic segments. A variation difference in $T_R$ (denoted '$DT_R$') is expected in normal segments because the systolic phase, which the $T_R$ interval essentially spans, shortens during stress test tachycardia. On the other hand, in chronically ischemic segments, the $DT_R$ value is typically small because there is not an adequate mechanical response to stress. Hence, the waveforms provided by the functional scanner 12 are normalized in amplitude, for example, between −1.0 and +1.0, filtered, and sampled, for example, 70 times over the period of one heart cycle. However, the process of normalization and concatenation can be formalized so that the order of input waveforms is always the same for various training routines or designs. As will be described, any arrangement of input waveforms and parameters is acceptable for the NN 22.

The signal processor 16 includes two data outputs that are delivered and stored by the database 20. The first data output 46 provides "value" data, such as thickness values, dimensional data, and radius data. The second output 48 provides the derived strain rate waveform.

The second output 48 communicates the original ECG waveform 50, strain data 52, strain rate data 54, and pressure data 56. The information provided by the data outputs 46, 48 is received and stored by the database 20 along with projection and segment information provided by the position tracker 18. The data compiled in the database 20 is then sent to the NN 22 and diagnostic interpretation unit 24 for analysis and classification.

Neurons (or nodes) are the basic processing elements of the NN 22. Each node includes a weight, a bias, a summing function, and an output function. As the number of neuron layers and combinations of output functions increase, more complex and nonlinear classification problems can be solved more quickly. As will be described with respect to FIG. 6, it is contemplated that several NN structures may be used with the NN 22. For example, a structure with one layer of nodes or a structure with two, three, or more layers of neurons may be used in the NN 22. However, in accordance with some embodiments of the present invention, it is recognized that a two layer NN design may perform faster and with less potential for error than a single layer design and also does not present any significant disadvantage to using a more complex layer structure, such as three or more layers in the NN 22. Accordingly, a preferred NN design includes a two-layer NN receiving 70 inputs (assuming that the sampling rate is 70 times over the period of one heart cycle) that feed into each layer of 5 nodes. Each 5 node layer then feeds an output layer of 1 node.

To properly analyze the data provided to the NN 22, the NN 22 must be "taught" to make interpretations. To accomplish this, an initial, "virgin" NN system is trained on representative data and given correct answers to "learn" appropriate interpretations. Initially, the entire longitudinal and transverse strain waveforms may be sampled equally with an additional measure of the duration of the heart cycle. A pruning process may be performed by examining the weights of the NN 22 as it continues to learn. Also, it is contemplated that the weights could be recovered and mapped to the inputs to the NN 22 to provide insights about the diagnostic importance of the individual inputs. In this manner, inputs/features that are contributing the least to the classification process may be removed. For example, features such as additional sampled waveforms or parameters including thickness, radius of curvature, heart rate, and the like can be removed as desired. However, once training starts, the data format and arrangement should be kept unchanged. As will be described with respect to FIG. 6, by training multiple NNs using a different number of inputs and then comparing the classification results on the same testing data, the learning process can also be advanced.

In any case, it is contemplated that backpropagation may be used for training. Backpropagation is used to calculate derivatives of performance (perf) with respect to the weight and bias variables (X). Each variable can be adjusted according to gradient descent with momentum, such that the change in a particular variable is found as follows:

$$dX = mc \cdot dx_{pre} + lr \cdot (1-mc) \cdot dpref/dX'$$

where $dX_{prev}$ is the previous change to the weight or bias, mc is the momentum constant, and lr is the learning rate. As is known in the art, the use of "momentum" when training a neural network reduces the probability that a backpropagation network will be caught in shallow minima. Training stops when any of the following conditions occur: 1) the maximum number of training cycles is reached, 2) the maximum amount of time has been reached, 3) performance has been minimized to a particular goal, or 4) the performance gradient falls below a set minimum.

Figure 4:
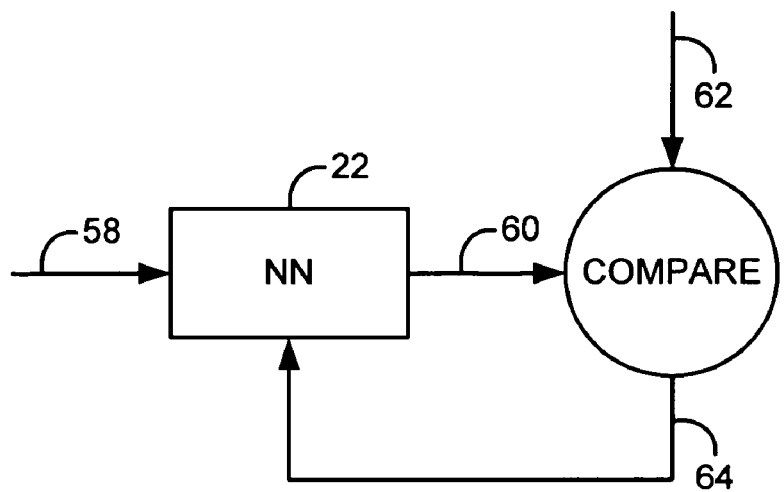
FIG. 4 is a flow chart setting forth the steps for training the trainable diagnostic system of FIG. 1.

As stated, it is contemplated that the NN 22 may be trained on representative waveforms and given correct answers (i.e., one of two output targets, such as +1 or −1) to "learn" appropriate classification of the input data. Referring now to FIG. 4, during this supervised learning process, a known input 58 is delivered to the NN 22. An output 60 of the NN 22 is collected and compared to a target response 62 expected based on the known input 58. By monitoring deviations from the target response 62, changes 64 in the weights and biases of the NN 22 are made to meet the given target response 62. Hence, the response of the NN 22 can be adjusted based on a comparison of the output 60 and the target 62 until the output 60 matches the target 62.

Unlike conventional NN designs, the inputs to the NN 22 of the present invention are not pre-determined parameters, such as peak values or timings to particular events, but individual landmark points (for example, 70) of the normalized waveforms sampled equidistantly during one cardiac cycle. For example, should the LV be divided into 18 segments, 2 waveforms with a sampling density of 70 landmark points per waveform would be used to represent mechanical performance within each segment, and that one input would be a variable (R-R interval duration). The NN 22 would, therefore, receive 18×2×70+1=2,521 inputs.

Referring again to FIG. 1, regardless of the exact number of inputs to the NN 22, the NN 22 analyzes the data received at each input, weights the data, and delivers the analyzed and weighted data to the diagnostic interpretation unit 24. In particular, the NN 22 analyzes each input received from the database 20 and, based on its training, "scores" the data along a scale ranging from highly indicative of an abnormal condition to highly indicative of a normal condition. A metric in the form of a clinical $DT_R$ measurement indicating the "score" of the current data is then delivered to the diagnostic interpretation unit 24 to "interpret" the score based on a variety of information.

The diagnostic interpretation unit 24 utilizes a Bayesian probabilistic approach to classify the data interpreted by the NN 22. Such a Bayesian probabilistic analysis approach is described in Bretthors GL. Bayesian spectrum analysis and parameter estimation. In: Berger J, Fienberg S, Gani J, Krickeberg K, Singer B (Eds.). Lecture notes in statistics. Springer-Verlag, New York, N.Y. 1988. In accordance with one embodiment, the diagnostic interpretation unit 24 receives the metric from the NN 22 and automatically assigns it to a class of 'normal' or 'abnormal' waveforms using the available distributions of the $DT_R$ parameter discussed above. In the most basic of operations, the higher the positive value, the higher the likelihood of a "normal" condition. On the other hand, the lower the negative value, the higher the likelihood of an "abnormal" condition.

However, as is the case in any distribution, while each standard deviation from the mean is more easily classifiable, there is a plurality of values that may fall into an area that is less easily classifiable. Accordingly, it is preferable that the diagnostic interpretation unit 24 support diagnostic categories including 'normal', 'uncertain', and 'abnormal', to better resemble human judgments that typically involve some level of uncertainty. However, unlike analysis techniques that rely on human judgment to classify the waveform, since the NN 22 is capable of analyzing all data available, the metric provided to the diagnostic interpretation unit 24 is a significantly more accurate "scoring" analysis than could be provided by an individual evaluating peaks or crossing points in a waveform. Furthermore, by using a Bayesian probabilistic analysis, the diagnostic interpretation unit 24 provides a highly sophisticated analysis of the metric provided by the NN 22 based on a large population of comparative data.

Figure 5:
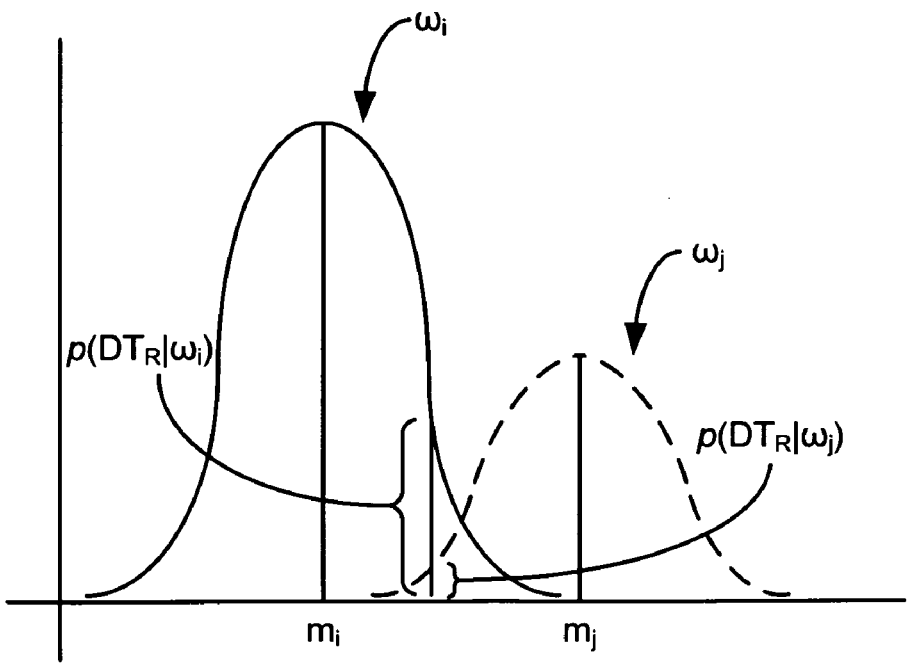
FIG. 5 is a graph illustrating the probability distributions used by the trainable diagnostic system assuming normal distributions of $DT_R$ in each diagnostic class.

Referring now to FIG. 5, exemplary probability distributions are illustrated where the solid distribution is attributable to normal cardiac waveforms and the dashed distribution is attributable to abnormal, or ischemic, waveforms. In this case, assuming diagnostic classes of $\omega_i$ from i=1 to i=m, where m is the range of a numerical classification scale (i.e., the number of categories), the diagnostic interpretation unit 24 determines the class to which a given LV segment with a given value of $DT_R$ belongs based on conditional probabilities. In particular, $p(\omega_i|DT_R)$ through $p(\omega_M|DT_R)$ is calculated, where $p(\omega_i|DT_R)$ gives the probability that the correct class is ωi for a given value of $DT_R$. Accordingly, classification is performed as:

$$DT_R \in \omega_i \text{ if } p(\omega_i|DT_R) > p(\omega_j|DT_R) \text{ for all } j \neq i.$$

Hence, a cardiac segment with a given value of $DT_R$ is predicted to be in class $\omega_i$ if $p(\omega_i|DT_R)$ is a maximum value. However, the probabilities of $p(\omega_i|DT_R)$ are unknown. Since representative data is collected in the database 20, that data is then used to estimate the probability density function of $DT_R$ in each of the classes wa (i.e., $p(DT_R|\omega_i)$).

Assuming normal distributions of $DT_R$ in each of the diagnostic classes wu, the desired $p(\omega_i|DT_R)$ and the estimated $p(DT_R|\omega_i)$ are related by the Bayesian theorem as:

$$p(\omega_i | DT_R) = \frac{p(DT_R | \omega_i)p(\omega_i)}{p(DT_R)},$$

where $p(\omega_i)$ is the prior probability of belonging to class $\omega_i$ and $p(DT_R)$ is the total probability density of finding myocardium with the observed value $DT_R$. Accordingly, the likelihood ratio is defined as the quantity:

$$L_{ij}(DT_R) = \frac{p(DT_R | \omega_i)}{p(DT_R | \omega_j)}.$$

Here, the values of $p(\omega_i)$ and $p(\omega_j)$ are called prior probabilities because they correspond to the probabilities of class memberships of a myocardial segment in the absence of data. Additionally, the values of $p(\omega_i|DT_R)$ and $p(\omega_j|DT_R)$ are posterior probabilities found from the Bayesian theorem. Therefore, the classification rule is:

$$DT_R \in \omega_i \text{ if } p(DT_R|\omega_i)p(\omega_i) > p(DT_R|\omega_j)p(\omega_j) \text{ for all } j \neq i,$$

where $p(DT_R)$ can be removed as a common factor. It is mathematically convenient if the classification rule defined above is applied as:

$$g(DT_R) = \ln\{p(DT_R|\omega_i) p(\omega_i)\} = \ln p(DT_R|\omega_i) + \ln p(\omega_i),$$

where ln is the natural logarithm. The classification rule can now be restated as:

$$DT_R \in \omega_i \text{ if } g_i(DT_R) > g_j(DT_R) \text{ for all } j \neq i,$$

The conceptual difference from simply assessing cutoff values can be illustrated by a review of the likelihood ratio (odds factor in favor of abnormality) values for $DT_R$ ranging from +10 to −50 by 5. The posterior probability of ischemia given a) prior odds of 1:1 (i.e., 50% probability) and b) prior odds 1:9 (ie, 10% prior probability) illustrate that, for values of $DT_R$ of −15 or "greater", even with prior odds of 1:9 against ischemia, the posterior probability of ischemia is 27% or more. Likewise, for values of $DT_R$ between −25 and −20, the likelihood is approximately 1 and the posterior probability with prior odds 1:1 ranges from approximately 40% to almost 60%. Additionally, for values of $DT_R$ of −30 or "less", even with prior odds of 1:1 (even odds) for ischemia (50% prior probability), the posterior probability of ischemia is approximately 27% or less. It should be noted that when $DT_R$ approaches −50, the posterior probability of ischemia paradoxically starts to increase. While this phenomenon is strongly dependent on the assumption of two Gaussian distributions (one dedicated to 'normal' conditions and the other dedicated to 'abnormal' conditions), and it would be advisable to not use the Gaussian model in this range of values, since this value of $DT_R$ rarely occurs under either assumption (i.e., normality or ischemia), it may be unnecessary to do so.

It should be noted that for reduced complexity, the above example utilizes only one parameter (i.e. $DT_R$) for analysis and classification. However, it is contemplated that more than one parameter may also be utilized. As such, assuming that the joint probability distribution of parameters is approximated by a multivariate Gaussian distribution, the maximum likelihood classifier can be generalized as:

$$gi(xi) = \ln p(\omega_i) - \frac{1}{2}\ln|\sum_i| - \frac{1}{2}(x_i - m_i)^T \sum_i^{-1} (x_i - m_i),$$

where $x_i$ is a data vector (the value of the parameters in a given cardiac segment), $m_i$ is the mean vector of the data in class $\omega_i$, and $\Sigma_i$ is the covariance matrix of the data in class $\omega_i$.

Referring again to FIG. 1, once the diagnostic interpretation unit 24 has classified the metric(s) received from the NN 22, the classified data is provided to the visualization unit 26. The visualization unit 26 also receives the unanalyzed data stored in the database 20. Using both sources of information, the visualization unit 26 generates a graphic representation that is sent to a display 28 for review by a technician or physician.

In accordance with one embodiment, the notification may simply communicate that the system 10 has determined the acquired data to be 'normal', 'abnormal' or 'inconclusive.' In accordance with another embodiment, the displayed graphic representation may be a highlighting of segments determined to be 'abnormal' or 'inconclusive' superimposed over the corresponding ultrasound image of the segment. Furthermore, color codes or hue variations may be utilized to communicate the severity of a segment determined to be 'abnormal' with differing color codes or hue variations used to communicate segments determined to be 'normal' or 'inconclusive.'

The waveform(s) evaluated in the above-described system is rich in information about local myocardial function throughout the cardiac cycle. As described, this information can be utilized to classify segments in a user-independent method as normal, abnormal, or even inconclusive/uncertain. Computer analysis of strain and strain rate patterns of deformation can utilize this information to aid physicians in the diagnosis of ischemia. Additionally, it is contemplated that the above-described system can be sufficiently flexible so that waveforms other than strain or additional input nodes can easily be added.

Figure 6:
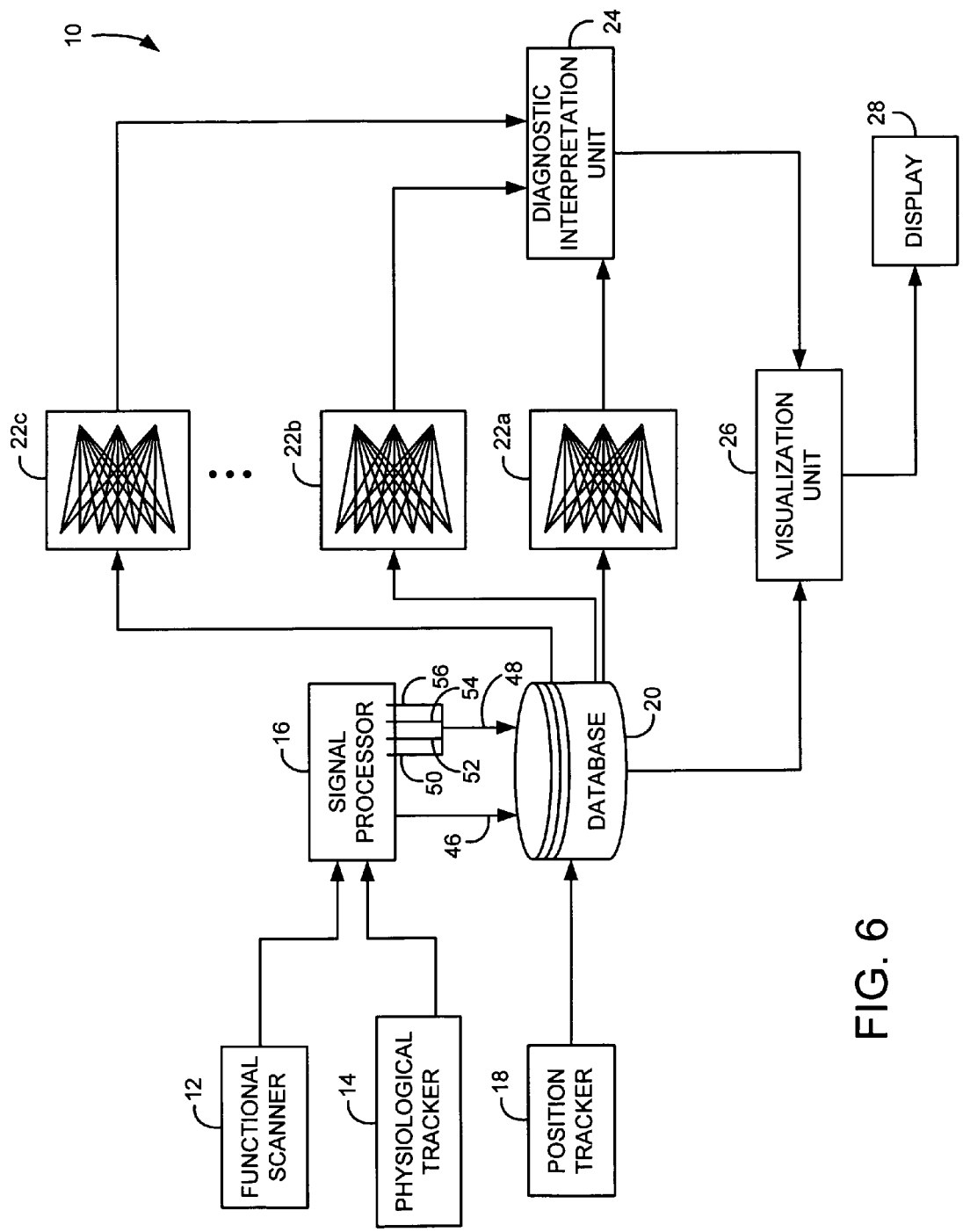
FIG. 6 is a schematic illustration of another embodiment of a trainable diagnostic system configured to receive waveforms from multiple contiguous segments and process the waveforms using dedicated neural networks trained for particular anatomical segments.

For example, referring now to FIG. 6, the above-described system 10 has been expanded to receive waveforms from three contiguous segments. In this regard, the waveforms from the three contiguous segments can be processed by dedicated neural networks 22a, 22b, 22c that are specifically trained for the appropriate anatomical segment being provided to each. In this regard, though only three networks are shown, it is contemplated that such a configuration could include at least eighteen individually trained and interconnected segmental NN modules for analysis of the left ventricle.

Again, each neural network 22a, 22b, 22c must be trained. In this regard, an iterative training process can be used. As described above, once training results meet the criteria for a given segment, training of another segment can begin. This loop of training, testing, pruning, re-training, and retesting continues for each segment. In the case of such segment-specific networks, each neural network 22a, 22b, 22c can be trained in parallel, where each neural network 22a, 22b, 22c is focused on respective segmental waveforms. In addition, it is contemplated that a network of segment specific networks can be used to represent relationships among the segments.

Therefore, the above-described system and method allows for the analysis of functional imaging data to determine indicators of various pathologies with increased speed and accuracy. More particularly, the use of a trained neural network and diagnostic interpretation unit allows for the evaluation of a full spectrum of functional imaging data, such as cardiac ultrasound images or entire echocardiogram waveforms, to determine indicators of pathologies such as ischemia with a speed and accuracy unattainable by traditional analysis techniques and systems.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A system for analyzing mechanical waveforms to identify a given pathology comprising:
    an instrument for acquiring a mechanical waveform from a subject during a functional cycle;
    a signal processor connected to receive the mechanical waveform from the instrument and normalize the mechanical waveform over at least one portion of functional cycle;
    a neural network coupled to the signal processor to receive an entirety of the mechanical waveform as a normalized mechanical waveform after processing by the signal processor and process the normalized mechanical waveform based on a plurality of weights selected by a training process that relates mechanical waveforms to a diagnostic outcome related to the given pathology, the neural network being operable to generate at least one metric indicating a degree of relation between the normalized mechanical waveform and the diagnostic outcome;
    a diagnostic interpretation module receiving the at least one metric from the neural network and classifying the mechanical waveform as at least one of indicative of the given pathology and not indicative of the given pathology based on a comparison of the at least one metric to at least one probability distribution of a likelihood of the given pathology; and
    wherein the mechanical waveform includes an echocardiographic waveform and the given pathology includes ischemic myocardium.

2. The system of claim 1 wherein the at least one metric includes a variation in a TR interval of in the echocardiographic waveform under an unstressed condition and a stressed condition.

3. The system of claim 1 further comprising a visualization module in communication with a display and wherein the diagnostic interpretation module communicates the classification of the at least one metric to the visualization module to generate a notification shown on the display communicating that the mechanical waveform acquired from the subject is indicative of a "normal" condition substantially free of the given pathology, an "abnormal" condition including the given pathology, and an "uncertain" condition that is inconclusive with respect to the given pathology.

4. The system of claim 1 further comprising a plurality of neural networks configured to receive a portion of the normalized mechanical waveform corresponding to a particular contiguous anatomical segment of the entirety of the mechanical waveform derived from the subject and wherein each neural network includes a respective plurality of weights specific to the corresponding anatomical segment of the received mechanical waveform.

5. The system of claim 1 wherein the at least one probability distribution includes a first Gaussian distribution of data associated with the given pathology and a second Gaussian distribution of data not associated with the given pathology.

6. The system of claim 1 wherein the neural network includes at least two layers of nodes and wherein each layer of nodes includes multiple nodes associated with each input and feeding an output layer with at least one node.

7. The system of claim 6 wherein the mechanical waveform includes at least one strain waveform normalized in amplitude and sampled over a period of one functional cycle by the signal processor to generate the normalized mechanical waveform and wherein each sample is fed into at least one of the multiple nodes associated with each input.

8. The system of claim 1 wherein the diagnostic interpretation module performs a Bayesian probabilistic analysis of the at least one metric generated by the neural network to classify the mechanical waveform.

9. A system for analyzing functional data including a mechanical waveform acquired during a cardiac cycle of a subject to identify an ischemic myocardium comprising:
- a signal processor connected to receive the mechanical waveform of the cardiac cycle of the subject, measure a TR interval of the cardiac cycle, and normalize the mechanical waveform based on a resting heart rate;
- a neural network having a plurality of weights determined based on pre-selected learning mechanical waveforms, receiving an entirety of the mechanical waveform as a normalized mechanical waveform from the signal processor, and processing the TR interval and the normalized mechanical waveform based on the plurality of weights to generate a measure of a change in the TR interval when the subject is subjected to stressed conditions and when the subject is subjected to unstressed conditions; and
- a diagnostic interpretation module receiving the measure of the change in the TR interval from the neural network and calculating a probability of the subject having ischemic myocardium based on the measure of the change in the TR interval when compared to at least one probability distribution related to individuals having ischemic myocardium; and
- wherein the diagnostic interpretation module classifies the mechanical waveform as at least one of 'normal', 'abnormal', and 'uncertain' based on the probability of the subject having ischemic myocardium.

10. The system of claim 9 further comprising visualization module receiving the classification of the mechanical waveform from the diagnostic interpretation module and communicating with a display to generate an indication of the classification.

11. The system of claim 9 wherein the diagnostic interpretation module performs a Bayesian probabilistic analysis of a measure of a change in a TR interval generated by the neural network to classify the mechanical waveform.

12. The system of claim 9 wherein the neural network includes at least two layers of nodes and wherein each layer of nodes includes multiple nodes associated with each input and feeding a single node at an output layer.

13. A method for diagnosing a cardiac condition comprising the steps of:
- acquiring an echocardiogram waveform from a heart of a subject during a cardiac cycle, the echocardiogram waveform being indicative of a deformation of the heart during the cardiac cycle;
- normalizing an entirety of the echocardiogram waveform with respect to a resting cardiac phase;
- applying the normalized echocardiogram waveform to a neural network that has been trained to recognize an indication of a given pathology in echocardiogram waveforms;
- determining a probable diagnosis that the subject is afflicted with the given pathology; and
- displaying the probable diagnosis.

14. The method of claim 13 wherein the given pathology includes ischemic heart disease.

15. The method of claim 13 wherein the step of determining a probable diagnosis is performed automatically by a diagnostic probability unit applying a Bayesian probabilistic analysis to a metric generated by the neural network using at least two Gaussian distributions.

16. The method of claim 13 wherein the step of normalizing the acquired echocardiogram waveform includes normalizing an amplitude of the acquired echocardiogram waveform with respect to the resting cardiac phase.

17. The system of claim 1 wherein the neural network has a multi-layer design, each layer including multiple nodes, that each feeds into an output layer.

18. The system of claim 1 wherein the at least one metric includes a variation difference in time to relaxation ($DT_R$) reflected in the mechanical waveform.

19. The system of claim 18 wherein the diagnostic interpretation module considers $DT_R$, is classified using the following relationship:

$$DT_R \in \omega_i \text{ if } p(\omega_i|DT_R) > p(\omega_j|DT_R) \text{ for all } j \neq i;$$

For diagnostic classes of $\omega_i$ from i=1 to i=m, where m is the range of a numerical classification scale, and $p(\omega_i|DT_R)$ gives the probability that the correct class is $\omega_i$ for a given value of $DT_R$.

* * * * *